United States Patent [19]

Lally

[11] Patent Number: 5,108,408
[45] Date of Patent: Apr. 28, 1992

[54] UTERINE-RING HYSTERECTOMY CLAMP

[76] Inventor: James J. Lally, 5760 Windsor Cir., Shawnee Mission, Kans. 66205

[21] Appl. No.: 511,777

[22] Filed: Apr. 20, 1990

[51] Int. Cl.⁵ .............................................. A61B 17/00
[52] U.S. Cl. .................................. 606/119; 606/157; 604/55
[58] Field of Search ................. 606/119, 157, 118; 605/55

[56] References Cited

U.S. PATENT DOCUMENTS

| 183,602 | 10/1876 | Strubell | 606/157 |
|---|---|---|---|
| 3,707,970 | 1/1973 | Smirnov | 606/119 |
| 4,000,743 | 1/1977 | Weaver | 606/119 |
| 4,022,208 | 5/1977 | Valtchev | 606/119 |
| 4,491,136 | 1/1985 | LeVeen | 606/118 |
| 4,644,953 | 2/1987 | Lahody et al. | 606/119 |

FOREIGN PATENT DOCUMENTS 0319394  6/1989  European Pat. Off. ............ 606/119

OTHER PUBLICATIONS

"An Atlas of Pelvic Operations", pp. 8-39, Langdon Parsons, M.D. and Howard Ulfelder, M.D.

Primary Examiner—Stephen C. Pellegrino
Assistant Examiner—Gary Jackson
Attorney, Agent, or Firm—Michael Yakimo, Jr.

[57] ABSTRACT

A surgical tool for use in abdominal hysterectomies includes an inner uterine-ring assembly having a ring for insertion into the vagina at the juncture of the cervix and vagina. An outer clamping assembly insertable through a surgically opened abdominal cavity is clamped about the inner ring with the vaginal tissue interposed therebetween. The combination presents a scalpel guide for surgical circumcision of the interposed tissue as well as controls undesirable bleeding from the circumcised tissue.

21 Claims, 4 Drawing Sheets

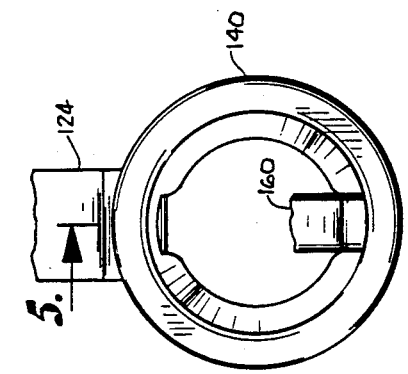
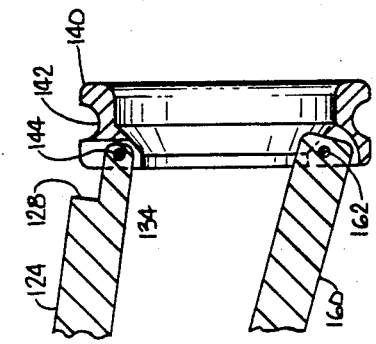
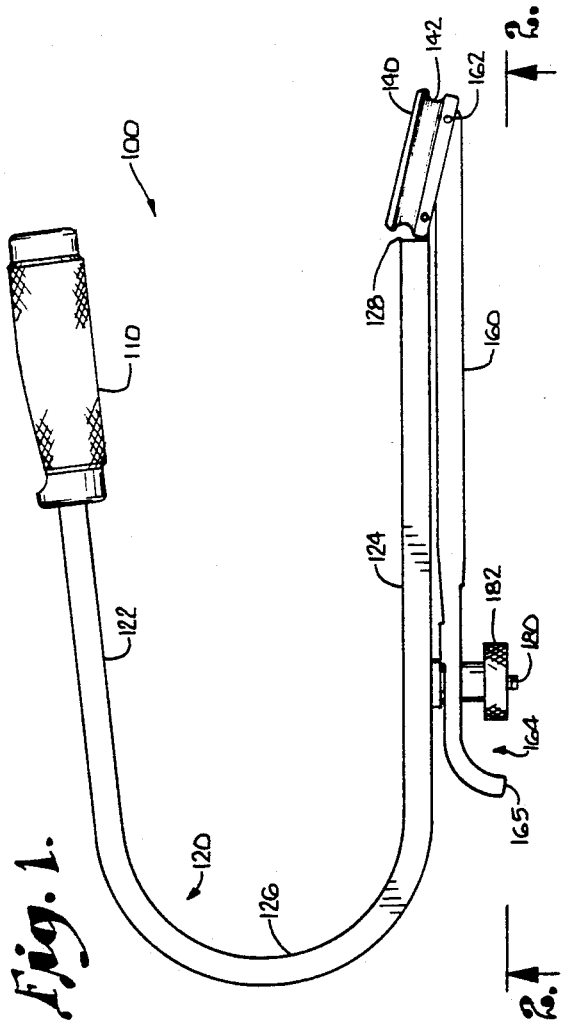
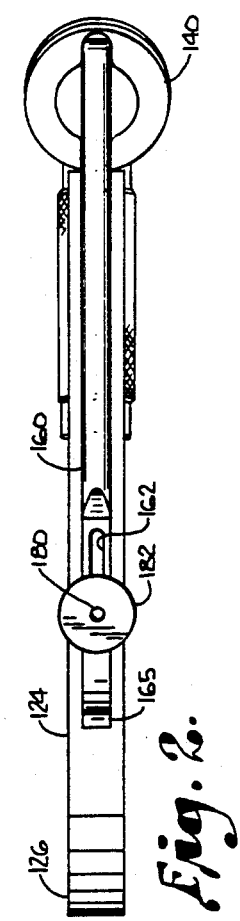

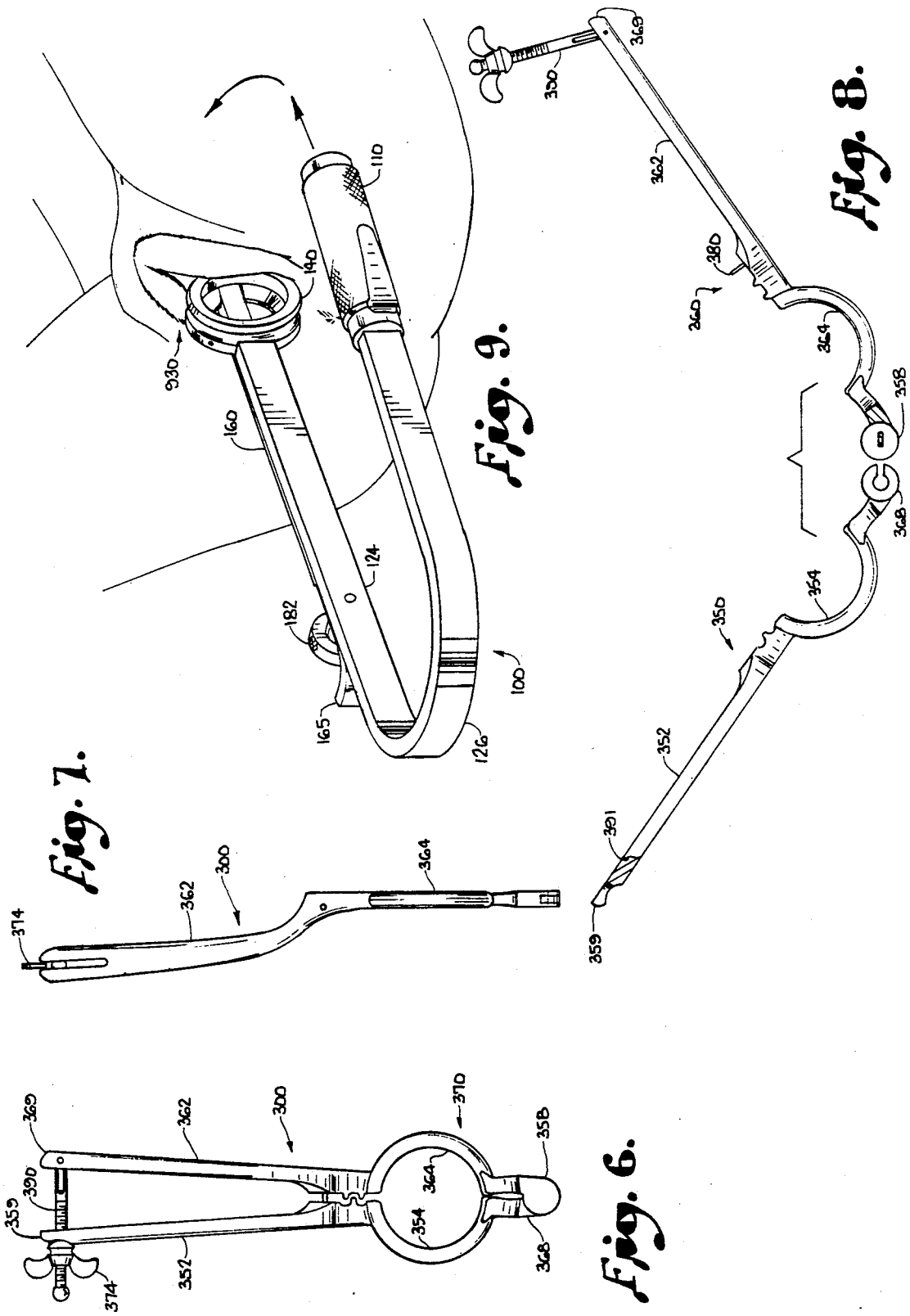

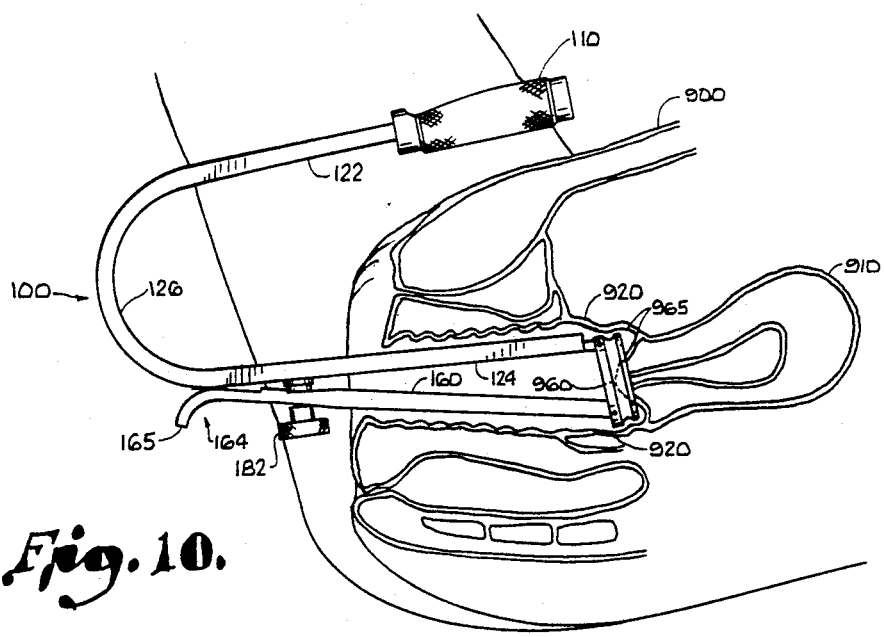
Fig. 10.
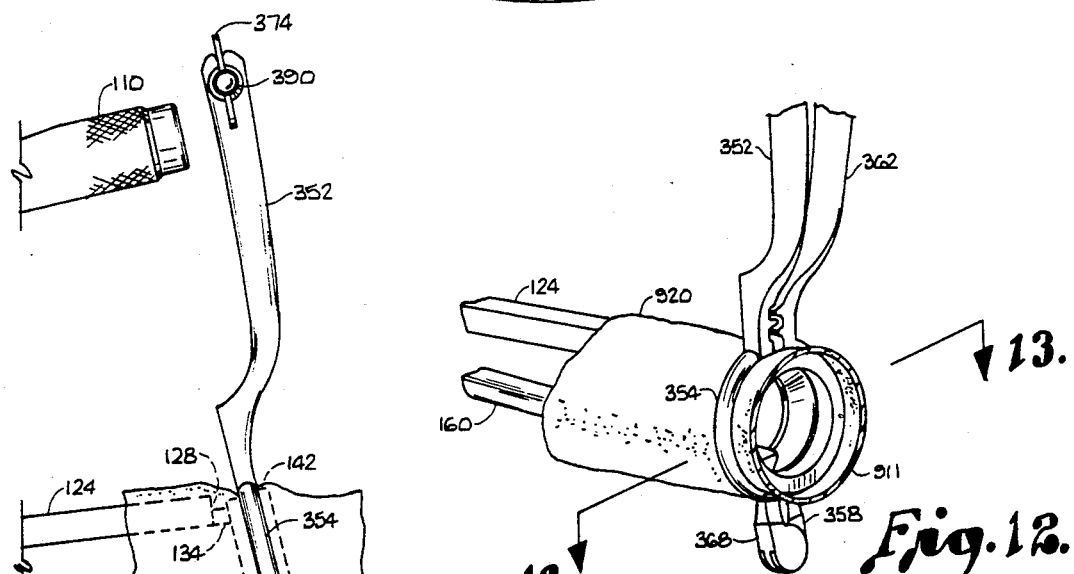
Fig. 11.
Fig. 12.
Fig. 13.

UTERINE-RING HYSTERECTOMY CLAMP

BACKGROUND OF THE INVENTION

This invention relates to a surgical device, and more particularly, to a surgical tool for use in performing abdominal hysterectomies.

The basic technique of an abdominal hysterectomy is well known in the medical art. Reference is made to U. S. medical references in which the steps in performing a hysterectomy are set forth therein. One such reference is "An Atlas of Pelvic Operations" published by W. B. Saunders Company and written by Langdon Parsons, M. D. and Howard Ulfelder, M. D. in 1968.

Basically, an incision is made in the abdominal wall and underlying peritoneum so as to expose the abdominal cavity and the various organs therein including the uterus. The uterus is to be removed at its cervical juncture with the vagina commonly referred to as the fornix. Upon identifying such juncture, surrounding blood vessels are ligated and circumcision is made about the vaginal wall at this fornix area. Upon removal of the uterus, the resulting vaginal edges are sewn shut.

Various problems arise in this general operation. The exact location of the vaginal fornix may be difficult to find in some patients. Moreover, constant attention must be made to bleeding due to the surrounding ligaments and blood vessels. Also, a clean, circular incision about the vaginal wall at the fornix may be difficult.

In response thereto I have invented a surgical tool for abdominal hysterectomies which comprises a rigid, inner ring for insertion into the vagina so as to rigidify and define the fornix area from within the vagina. An outer ring is clamped about this inner ring with the vaginal wall therebetween prior to the above circumcision. This rigid ring further presents a guide for scalpel circumcision about the vaginal wall by the surgeon. The clamping assembly precludes undesirable bleeding from the surrounding blood vessels upon circumcision. Subsequent to the circumcision and uterus removal, the blood vessels are then ligated and the clamp easily removed. The resulting annular edge of the vagina is then sutured together.

My surgical device defines a fornix area and provides a rigid guide to the surgeon to allow for a proper vaginal circumcision. Furthermore, undesirable bleeding from the surrounding blood vessels can be controlled due to the relationship between the outer clamping ring and inner ring assemblies.

Accordingly, it is a general object of this invention to provide a surgical tool for use in hysterectomy operations.

Another object of this invention is to provide a surgical tool, as aforesaid, which rigidly defines and outlines the vaginal fornix.

Still another object of this invention is to provide a surgical tool, as aforesaid, which provides a guide to the surgeon for circumcision of the vaginal wall at the fornix area.

Another object of this invention is to provide a surgical tool, as aforesaid, which controls hemostatic pressure and precludes bleeding from surrounding ligaments and blood vessels during and after said circumcision.

Another object of this invention is to provide a surgical tool, as aforesaid, which comprises inner and outer ring assemblies which are easily adaptable for insertion into and withdrawal from a patient.

Other objects and advantages of this invention will become apparent from the following description taken in connection with the accompanying drawings, wherein is set forth by way of illustration and example, an embodiment of this invention.

BRIEF DESCRIPTION OF THE DRAWINGS

FIG. 1 is a side elevation view showing the inner uterine-ring assembly in a collapsed position;

FIG. 2 is a bottom plan view, taken along line 2—2 in FIG. 1, illustrating the locking device for holding the inner uterine-ring in position;

FIG. 3 is a fragmentary view illustrating the inner uterine-ring in an open, functional position normal to the collapsed FIG. 1 position;

FIG. 4 is an elevation view, on an enlarged scale, as viewed along line 4—4 in FIG. 3;

FIG. 5 is a sectional view, taken along line 5—5 in FIG. 4, illustrating the pivotal attachments of the inner uterine-ring to the shaft and linkage arm;

FIG. 6 is an elevation view showing the outer clamping assembly;

FIG. 7 is a side elevation view of the outer clamping assembly in FIG. 6;

FIG. 8 is a view of the clamping ring assembly of FIG. 6 and showing the assembly in an exploded mode;

FIG. 9 is a diagrammatic view showing alignment of the inner uterine-ring with the vaginal opening of the patient prior to penetration;

FIG. 10 is a diagrammatic view illustrating the inner uterine-ring in a functional, open position and in place at the fornix area of the patient;

FIG. 11 is a fragmentary view, on an enlarged scale, illustrating the outer clamping ring in a clamped position about the inner uterine-ring with a portion of the vaginal canal interposed therebetween;

FIG. 12 is a perspective view showing the outer uterine-ring in place about the inner uterine-ring with the vaginal canal being clamped therebetween subsequent to circumcision;

FIG. 13 is a sectional view taken along line 13—13 in FIG. 12, illustrating the relationship between the inner and outer uterine-rings with vaginal tissue therebetween.

DESCRIPTION OF THE PREFERRED EMBODIMENT

Figure 14:
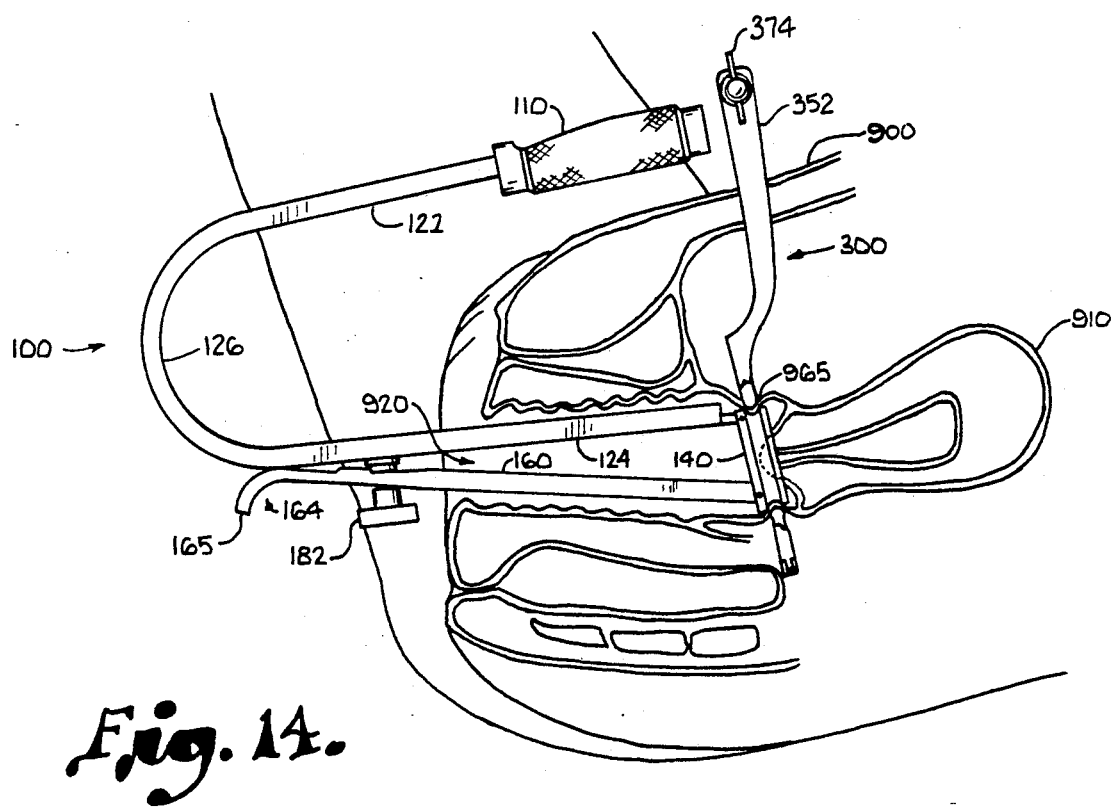
FIG. 14 is a diagrammatic view, similar to FIG. 10, illustrating the insertion of the clamping assembly into the surgically opened abdominal cavity and about the inner uterine-ring with the fornix area of the vagina therebetween.

Turning more particularly to the drawings, FIGS. 1-14 illustrate the hysterectomy surgical device. The device includes an inner uterine-ring assembly 100 shown in FIG. 1. This assembly 100 comprises an upper handle 110 having a generally C-shaped frame 120 extending therefrom. This frame 120 presents a pair of generally horizontal, vertically-displaced struts 122, 124 connected by an integral/curved shank 126. The strut/shaft 124 has a distal end 128 with a mounting flange 134 extending therefrom. An inner uterine-ring 140 having an annular slot 142 is pivotally mounted to arm 134 by means of at least one pivot pin 144 extending through the ring 140 and into mounting flange 124.

Extending from the bottom of ring 140 is a linkage arm 160 pivotally mounted to ring 140 by means of pin 163. The linkage arm 160 extends along the underside of the shaft 124 as illustrated in FIG. 1. A slot 162 extends along the user/proximal end 164 of arm 160. The proximal end 164 presents a user-operable handle 165. Extending through slot 162 and from shaft 124 is a threaded pin 180 having a knob 182 attached thereto. Threadable movement of knob 182 along the extent of the threaded pin 180 enables pressure to be exerted against the arm 160. This pressure maintains pin 180 at a user-selectable position along the extent of slot 162 and thus maintains the position of ring 140. Upon displacement of the knob 182 from the arm 160 longitudinal movement of the arm 160 relative to shaft 124 is allowed. The extension of pin 180 through the slot 162 defines the extent of such longitudinal movement and thus the range of pivotal movement of ring 140. As such, the surgeon grasps the handle 165 of the linkage arm 160 and pivots the ring 140 between a collapsed, FIG. 1 position to a functional, FIG. 3 position generally normal to the FIG. 1 position. The ring 140 is then held at either position by exerting pressure of the knob 182 on the arm 160.

For use with this inner uterine-ring assembly 100 is an outer uterine-ring clamp assembly 300. This assembly generally comprises a pair of jaw-like clamps 350, 360. Each respective clamp 350, 360 comprises a handle 352, 362 having a generally semi-circular jaw/ring 354, 364 at the distal end thereof. Upon interlock between the male 358 and female 368 locking elements the rings 354, 364 form an outer uterine-ring 370 upon drawing the handles 352, 362 together (FIG. 6). A threaded pin 390 extends between the proximal ends 359, 369 of each handle 352, 362. Wing nut 374 engages the free end of the pin 390 so as to maintain the pin 390 in slot 391 and lateral displacement between the proximal ends of the respective handles 352, 362. Pin 380 extends from one of the handles so as to preclude full closure of the jaws 354, 364 which form the outer ring 370.

In use the patient is positioned in a conventional manner for hysterectomy operations. An incision is made in the abdominal wall 900 according to conventional medical procedure so as to properly expose the reproductive organs, i.e. the uterus 910, which are to be removed. As shown in FIGS. 10 and 14, the uterus 910 and outer vagina wall 920 are exposed to the surgeon.

It is recognized that certain conventional surgical steps are first performed in preparation for removing the uterus 910.

As illustrated in FIG. 9, the inner uterine-ring assembly 100 is positioned in a collapsed mode for initial insertion into the vagina 920 of the patient. The collapsed uterine-ring 140 is generally vertically aligned (FIG. 9) with the vaginal opening 930 so as to enhance this initial penetration. Subsequent to insertion, the shaft 124 positions the uterine-ring 140 in the vaginal canal at the juncture of the cervix 960 with the vagina identified as the fornix 965. The assembly 100 is rotated from a FIG. 9 position to a FIG. 10 position such that the handle 110 is positioned atop the abdominal wall of the patient as shown in FIG. 10. The surgeon, via linkage arm 140, pivots the ring 140 about 90 degrees from its collapsed position to a functional, generally vertical position as shown in FIG. 10. This position is then maintained by tightening knob 182 so as to bear against the linkage arm 160 as above described. Once the uterine-ring 140 is positioned, it can be further adjusted so that it is placed in the desired position at the fornix 965, i.e. the point at which the surgical circumcision is to be made. The protrusion of the cervix 960 into ring 140 delimits further penetration of the ring 140 into the vaginal canal. This position is tactilely sensed by the surgeon. Thus, the junction 965 of the vagina and uterus is rigidified, supported and exposed to the surgeon. Once so positioned, a rigid, circular area of the vagina is defined and presented to the surgeon.

Subsequently, after clearance of surrounding ligaments and vessels the outer clamping assembly 300 is clamped about this uterine-ring 140 with the tissue of the vagina interposed therebetween. The respective clamps 350, 360 may be separated to allow for insertion of the semi-circular rings 354, 364 into the abdominal cavity about the vagina and about this inner uterine-ring 140. Upon interlock of mating elements 358, 368 the resulting ring 370 encompasses this inner uterine-ring 140 with hemostatic pressure on the vaginal tissue and surrounding blood vessels therebetween. Thus, the clamped blood vessels need not be cut away as in a normal procedure. The hemostatic pressure afforded by the resulting ring 370 is controlled by variable displacement of the handles 352, 362 as regulated by the threaded pin 390/wing nut 374 engagement as above described.

As shown in FIGS. 11-13, this combination of assemblies 100, 300 presents a guide to the surgeon for scalpel circumcision of the clamped tissue. The scalpel (not shown) is drawn about the annular groove 142 of the inner uterine-ring 140 as further guided by the rings 354, 364 embedded therein. On completion of the circumcision, the uterus 910 is separated from the vagina. The pressure of the clamping assembly 300 on the vaginal tissue precludes undesirable bleeding from the surrounding blood vessels and ligaments. The surrounding blood vessels, now visible in the sectioned free edge of the vaginal cuff, firmly held in the clamping assembly, are now hemostased with suture or cautery in a conventional manner. Once ligated, pressure on the clamping assembly 300 is partially reduced by handle displacement to allow the surgeon to check for undesirable bleeding from the ligated blood vessels and tissues. When all bleeding vessels are completely hemostased the clamping assembly 300 is then removed. The ring 140 of the inner uterine-ring assembly 100 is then positioned in a collapsed mode and removed from the patient. Upon such removal, the free annular end 911 of the vaginal canal are sutured together in a conventional manner. The sutured vaginal walls in turn are sutured to the round ligaments before peritonealization is completed.

The use of the inner uterine-ring 100/outer uterine ring 3300 combination as above described allows for an effective circumcision of the vaginal tissues. This circumcision presents a free end of the vaginal canal which is easily sewn together in a conventional manner. The clamping assembly 300 further allows the surgeon to ensure that there is no undesirable bleeding from the surrounding vessels. Subsequent to such circumcision these vessels ar easily ligated.

It is understood that the details of this hysterectomy operation have not herein been described as is well known by practicing surgeons. Accordingly, I have described the use of my instrument in connection with these well-known surgical procedures in order to advise those skilled in the art as to how my invention is to be utilized.

Although I have presented a preferred embodiment of my invention, it is to be understood that my invention is not to be restricted thereto, except as set forth in the following claims and allowable functional equivalents thereof.

Having thus described the invention, what is claimed as new and desired to be secured by Letters Patent is:

1. A surgical device for use in performing abdominal hysterectomies comprising:
   inner ring means for insertion with a vagina said means comprises:
   a ring;
   an elongated arm;
   means for attaching said ring to said arm, said arm having an end for presenting a handle allowing for user insertion of said ring into said vagina;
   clamp means for insertion into an exposed abdominal cavity and about the ring with a portion of said vagina therebetween;
   said ring and said clamp means providing a guide for a scalpel for circumcision of said vagina clamped about said ring.

2. The device as set forth in claim 1, wherein said attaching means comprises means for pivotally mounting said ring to an end of said arm.

3. The device as set forth in claim 2, further comprising linkage means for inducing said pivotal movement of said ring by a user.

4. The device as set forth in claim 3, wherein said linkage means comprises:
   a second arm;
   means for mounting said second arm to said ring, said second arm presenting a user-operable end wherein user movement of said arm end pivots said ring.

5. The device as set forth in claim 4, wherein said ring is pivotal between a first position in which said ring is generally aligned with an opening of said vagina and a second position in which said ring is generally normal to said first position.

6. The device as set forth in claim 5 further comprising locking means for maintaining said second arm and ring in a user-selectable position.

7. The device as set forth in claim 1, wherein said clamp means comprises:
   outer ring means having a configuration adapted to fit about said inner ring means;
   means for regulating the degree of said fit of said outer ring means about said inner ring means with said vagina clamped therebetween.

8. The device as set forth in claim 7, wherein said outer ring means comprises:
   a first element having a ring portion thereon for fitting about said inner ring means;
   a second element having a ring portion thereon for fitting about said outer ring means;
   means for releasably attaching said first ring element to said second ring element;
   said joined elements generally forming a ring circumscribing said inner ring means.

9. The device as set forth in claim 8, wherein said releasable attaching means comprises:
   a handle extending from said respective first and second ring elements; and
   means for controlling the displacement between said handles, said displacement varying the degree of fit of said ring elements about said inner ring means.

10. The device as set forth in claim 9, wherein said controlling means comprises:
    a pin extending between said handles, said pin having at least one free end extending through one of said handles;
    fastener means releasably engageable with said pin free end along the length thereof, said engagement precluding movement of said handle towards said free end of said pin, whereby to control said displacement between said handles.

11. The device as set forth in claim 10, wherein said pin is threaded and said fastener means comprises a nut engageable with said threads, said nut releasably engageable along the extent of said pin.

12. A surgical device for use in performing a hysterectomy comprising:
    shaft for insertion into a vagina;
    a ring element for insertion into said vagina;
    means for pivotally mounting said ring to said shaft;
    means for user manipulation of said ring between a first position aligning said ring with an opening to said vagina prior to said insertion and a second position generally normal to said first position subsequent to said insertion, said second position of said ring providing a guide for a cutting element for surgical circumcision of vaginal tissue surrounding said ring.

13. The device as set forth in claim 12, wherein said user-manipulation means comprises:
    a rod for insertion into said vagina with said shaft;
    means for mounting said rod to said ring,
    said rod presenting a user-operable end upon said vaginal insertion, whereby movement of said end pivots said ring.

14. The device as set forth in claim 13, further comprising locking means for precluding said rod movement, whereby to maintain said ring in at least one of said positions.

15. The device as set forth in claim 14, wherein said locking means comprises:
    a slot at said user-operable end of said rod;
    a pin attached to said shaft and extending through said slot;
    means for holding said pin at a position along said rod slot, said means precluding relative movement between said rod and said pin.

16. The device as set forth in claim 15, wherein said holding means comprises a fastener releasably engageable with said pin to preclude said relative movement therebetween.

17. The device as set forth in claim 16, wherein said fastener is a nut releasably engageable with threads on said pin.

18. The device as set forth in claim 12 further comprising:
    clamping means for engaging said ring with said vagina interposed therebetween,, said clamping means delimiting bleeding from said vagina upon said circumcision.

19. The device as set forth in claim 18, wherein said clamping means comprises:
    outer ring means adapted to fit about said ring with said tissue therebetween.

20. The device as set forth in claim 19 wherein said outer ring means comprises jaw means adapted to fit about said inner ring with said tissue therebetween.

21. A surgical device for use in performing abdominal hysterectomies comprising:
    clamp means for insertion into an exposed abdominal cavity and about a vagina at a position for subsequent surgical circumcision of said vagina, said clamp means comprising at least one jaw element;

a ring insertable into said vagina for providing a clamping surface, said ring rigidifying said vagina at said position for engagement by said clamp means, said at least one jaw element of said clamp means engaging said ring with said vagina interposed therebetween, said engagement precluding bleeding from said vagina position subsequent to said circumcision.

* * * * *

UNITED STATES PATENT AND TRADEMARK OFFICE
CERTIFICATE OF CORRECTION

PATENT NO. : 5,108,408
DATED : April 28, 1992
INVENTOR(S) : James J. Lally

It is certified that error appears in the above—identified patent and that said Letters Patent is hereby corrected as shown below:

Column 2, line 66, delete "134" and substitute --124--.

Column 2, line 67, delete "124" and substitute --134--.

Column 5, line 10, delete "with" and substitute --within--.

Column 5, line 55, delete "outer" and substitute --inner--.

Column 6, line 55, delete "therebetween,," and substitute --therebetween,--.

Signed and Sealed this

Twentieth Day of July, 1993

Attest:

MICHAEL K. KIRK

Attesting Officer      Acting Commissioner of Patents and Trademarks